United States Patent
Cho et al.

(10) Patent No.: US 8,440,313 B2
(45) Date of Patent: May 14, 2013

(54) CROSSLINKABLE THERMOSET MONOMER, COMPOSITION FOR PRODUCING PRINTED CIRCUIT BOARD COMPRISING THE THERMOSET MONOMER AND PRINTED CIRCUIT BOARD USING THE COMPOSITION

(75) Inventors: Chung Kun Cho, Suwon-si (KR); Myung Sup Jung, Seongnum-si (KR); Mahn Jong Kim, Daejeon (KR); Jin Young Bae, Seoul (KR); Chung Won Park, Daejeon (KR)

(73) Assignees: Samsung Electronics Co., Ltd. (KR); Samsung Electro-Mechanics Co., Ltd. (KR); Samsung Fine Chemicals Co., Ltd. (KR); Sungkyunkwan University Foundation For Corporate Collaboration (KR)

( * ) Notice: Subject to any disclaimer, the term of this patent is extended or adjusted under 35 U.S.C. 154(b) by 686 days.

(21) Appl. No.: 12/332,931

(22) Filed: Dec. 11, 2008

(65) Prior Publication Data
US 2009/0308643 A1 Dec. 17, 2009

(30) Foreign Application Priority Data
Jun. 13, 2008 (KR) .......................... 10-2008-0056003

(51) Int. Cl.
*B32B 15/08* (2006.01)
*B32B 15/20* (2006.01)
*C08L 49/00* (2006.01)

(52) U.S. Cl.
USPC ........... 428/458; 428/461; 428/901; 525/445; 525/534; 564/156

(58) Field of Classification Search ....................... None
See application file for complete search history.

(56) References Cited

U.S. PATENT DOCUMENTS
4,943,606 A * 7/1990 Inoue et al. .................. 523/457

FOREIGN PATENT DOCUMENTS
JP 2007-119610 5/2007

OTHER PUBLICATIONS

Watanabe et al. "Synthesis of New Ethynylene-Containing Aromatic Polyamides by Palladium-Catalyzed Polycondensation of Aromatic Diiodides with Aromatic Diethynyl Compounds Having Amide Units" Journal of Polymer Science Part A: Polymer Chemistry, vol. 33(14), 2385-2391 (1995).*
Machine Translation of JP 2007-119610 A (2007).*
Machine Translation of JP 2008-222690 A (2008).*

* cited by examiner

*Primary Examiner* — Ramsey Zacharia
(74) *Attorney, Agent, or Firm* — Cantor Colburn LLP

(57) ABSTRACT

Disclosed herein is a crosslinkable thermoset monomer. The crosslinkable thermoset monomer has acetylene groups as crosslinking groups introduced at both ends of the backbone. Also disclosed herein is a composition for producing a printed circuit board which comprises the crosslinkable thermoset monomer. The composition exhibits excellent mechanical and thermal properties. Therefore, the composition can be used as a material for next-generation boards that are becoming lighter in weight and smaller in size and thickness. Also disclosed herein is a printed circuit board using the composition.

18 Claims, 6 Drawing Sheets

- - - - -  Liquid crystal polymer

———— Crosslinkable thermoset monomer

- - - - -  Liquid crystal thermoset oligomer

———— Crosslinkable thermoset monomer

CROSSLINKABLE THERMOSET MONOMER, COMPOSITION FOR PRODUCING PRINTED CIRCUIT BOARD COMPRISING THE THERMOSET MONOMER AND PRINTED CIRCUIT BOARD USING THE COMPOSITION

This application claims priority to Korean Patent Application No. 10-2008-56003, filed on Jun. 13, 2008, and all the benefits accruing therefrom under U.S.C. §119 the contents of which in its entirety are herein incorporated by reference.

BACKGROUND

1. Field

This disclosure is directed to a crosslinkable thermoset monomer, a composition for producing a printed circuit board comprising the crosslinkable thermoset monomer, and a printed circuit board using the composition. More specifically, the crosslinkable thermoset monomer has acetylene groups as crosslinking groups introduced at both ends of the backbone.

2. Description of the Related Art

Recent advances in information and communication technologies have transformed our society into a high-tech communication and information society. The trend toward miniaturization and high performance of electronic devices, for example, mobile phones and personal computers, has led to high-density integration of printed circuit boards as essential elements of the electronic devices. Such high-density integration has mainly been achieved by layering printed circuit boards, reducing the thickness of printed circuit boards, making the diameter of through-holes smaller and reducing the interval of holes. Under these circumstances, there is a need for novel board materials with higher performance.

The use of high operating frequencies for rapid processing of much information in electronic information devices such as computers involves the problems of transmission loss and signal delay. Generally, a signal delay in a printed circuit board increases linearly with the square root of the relative permittivity of an insulating material around interconnection lines. Thus, low-permittivity board materials are needed to produce boards requiring a high transmission rate.

Liquid crystal polyester resins are board materials that have a dielectric constant as low as 3.0 and exhibit excellent characteristics, such as high heat resistance and low moisture absorption. The production of boards using liquid crystal polyester resins is dependent on melting processes, such as injection molding, because most of the liquid crystal polymers are insoluble or slightly soluble in solvents. However, a printed circuit board produced by injection or extrusion using a liquid crystal polymer is highly anisotropic due to the orientation of the polymer chains, causing difficulty in designing a circuit and poor mechanical properties.

Bismaleimide-triazine ("BT") and glass epoxy resins (e.g., ("FR-4") are currently used as typical board materials. However, these materials are not successful in providing satisfactory results, such as excellent mechanical properties, low permittivity, high heat resistance, low thermal expansion and low moisture absorption, for future packaging technologies. Thus, there is a need to develop novel materials that can meet the requirements for next-generation boards.

SUMMARY

Disclosed herein is a crosslinkable thermoset monomer having acetylene groups as crosslinking groups introduced at both ends of the backbone, represented by Formula 1:

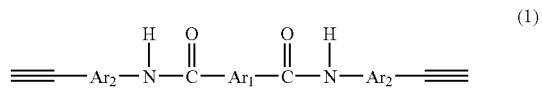

wherein $Ar_1$ and $Ar_2$ are each independently a divalent aromatic organic group including at least one structural unit selected from the group consisting of

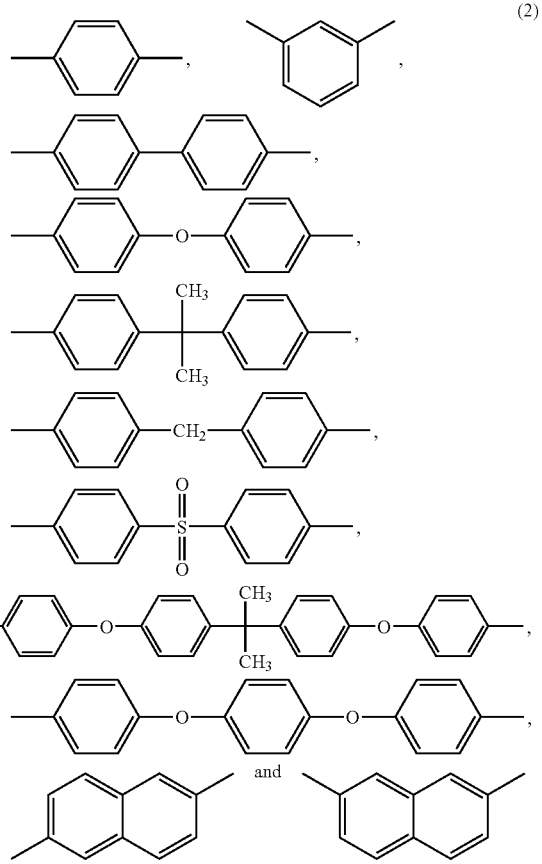

The crosslinkable thermoset monomer exhibits high crosslinkability.

Disclosed herein is a composition for producing a printed circuit board, which comprises the crosslinkable thermoset monomer.

For example, the composition is a suitable material for the production of a board with improved mechanical properties and thermal properties.

Disclosed herein is a printed circuit board using the composition.

The printed circuit board has, for example, good heat resistance, superior mechanical properties and improved handling properties.

BRIEF DESCRIPTION OF THE DRAWINGS

Exemplary embodiments will be more clearly understood from the following detailed description taken in conjunction with the accompanying drawings, in which.

DETAILED DESCRIPTION

Figure 1:
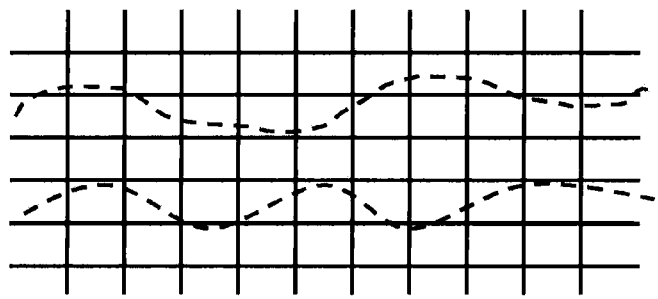
FIG. 1 is an exemplary schematic diagram illustrating a structure after a composition comprising a crosslinkable thermoset monomer, a soluble liquid crystal polymer and a solvent is applied to a substrate and cured.

Hereinafter, a detailed description will be given of exemplary embodiments with reference to the accompanying drawings.

It will be understood that when an element or layer is referred to as being "on," "interposed," "disposed," or "between" another element or layer, it can be directly on, interposed, disposed, or between the other element or layer or intervening elements or layers may be present.

It will be understood that, although the terms first, second, third, and the like may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, first element, component, region, layer or section discussed below could be termed second element, component, region, layer or section without departing from the teachings of the present invention.

As used herein, the singular forms "a," "an" and "the" are intended to comprise the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In one exemplary embodiment, there is provided a crosslinkable thermoset monomer having acetylene groups as crosslinking groups introduced at both ends of the backbone, represented by Formula 1:

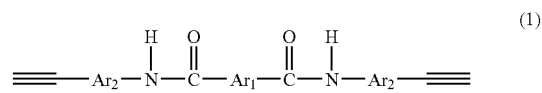

wherein $Ar_1$ and $Ar_2$ are each independently a divalent aromatic organic group including at least one structural unit selected from the group consisting of

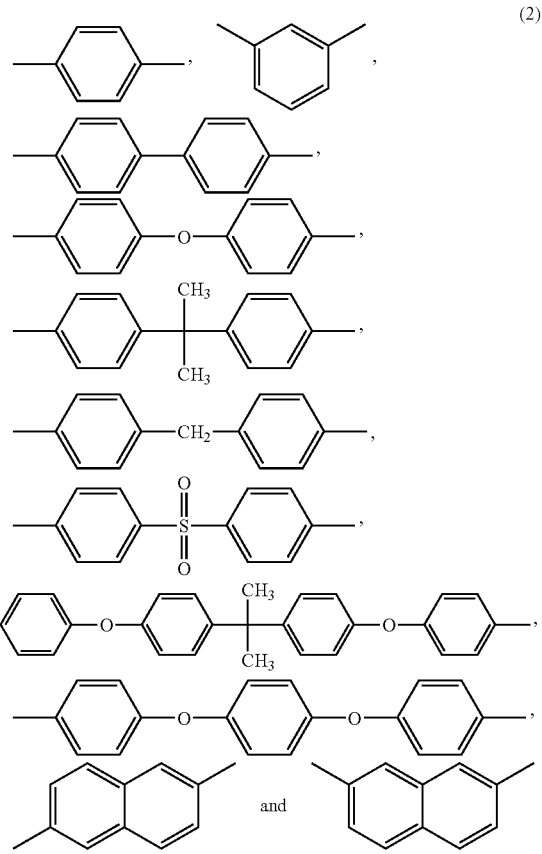

Due to the presence of the amide groups, the crosslinkable thermoset monomer is highly soluble in solvents and is cured at relatively low temperatures. In addition, the aromatic structures (particularly, biphenyl or naphthalene structures) of the crosslinkable thermoset monomer is preferred in forming a liquid crystal.

An exemplary synthesis procedure for the preparation of the crosslinkable thermoset monomer is explained below. First, a three-neck round-bottom flask equipped with a dropping funnel is flame-dried to remove moisture contained therein. 4-Ethynylaniline is dissolved in N-methyl-2-pyrrolidinone in the flask, and then triethylamine is added thereto.

The mixture is dissolved with stirring at room temperature for 10 minutes. To the solution is added dropwise a solution of terephthaloyl dichloride in N-methyl-2-pyrrolidinone through the dropping funnel over a period of 10 minutes. The resulting mixture is allowed to react with stirring for 30 minutes. After completion of the reaction, an aqueous HCl solution is added to the reaction solution to remove unreacted 4-ethynylaniline and salts, and the resulting mixture is passed through filter paper. The filtered crude product is washed with an aqueous NaHCO₃ solution to remove unreacted terephthaloyl dichloride, washed with deionized water, and dried to afford the desired crosslinkable thermoset monomer.

In another exemplary embodiment, the invention provides a crosslinkable thermoset monomer represented by Formula 3, 4 or 5:

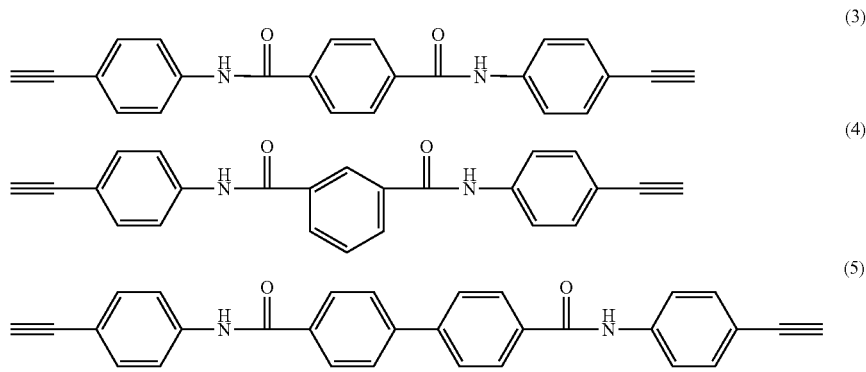

In another exemplary embodiment, there is provided a composition for producing a printed circuit board, which comprises a crosslinkable thermoset monomer and a soluble liquid crystal polymer ("LCP") or a soluble liquid crystal thermoset oligomer.

The crosslinkable thermoset monomer has acetylene groups as crosslinking groups at both ends of the backbone, represented by Formula 1:

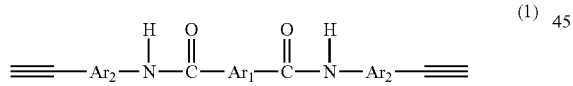

wherein $Ar_1$ and $Ar_2$ are each independently a divalent aromatic organic group including at least one structural unit selected from the group consisting of

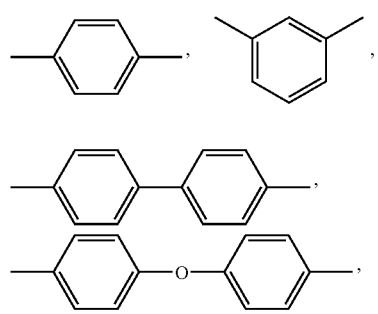

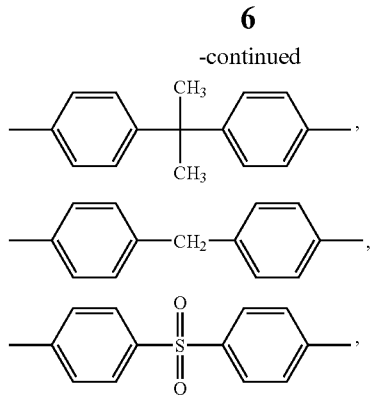

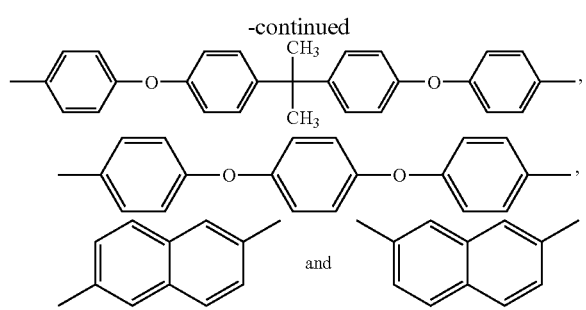

Since the liquid crystal polymer or the liquid crystal thermoset oligomer for use in the production of a board is highly viscous, it is difficult to dissolve a sufficient amount of the liquid crystal polymer or the liquid crystal thermoset oligomer in a solvent. The crosslinkable thermoset monomer is blended with the liquid crystal polymer or the liquid crystal thermoset oligomer in a suitable solvent to increase the solids content of the composition. Then, the composition is formed into a thin film and cured to produce a board. As a result, the solids content of the board can be increased. The use of the crosslinkable thermoset monomer reduces the production cost as well as imparts high heat resistance to the board. The glass transition temperature of the board using the composition disappears or is at least 300° C. Further, the board has a coefficient of temperature expansion of 10 ppm or less. Based on these characteristics, the composition can be used as a board material necessary for packaging of electronic devices that are becoming lighter in weight and smaller in size and thickness.

The crosslinkable thermoset monomer and the soluble liquid crystal polymer or the soluble liquid crystal thermoset oligomer are preferably present in a weight ratio of 5:95 to 70:30. If the crosslinkable thermoset monomer is present in an amount of less than 5% by weight, sufficient crosslinking effects are not obtained. Meanwhile, if the crosslinkable thermoset monomer is present in an amount exceeding 70% by weight, it becomes brittle, making it difficult to use the composition.

Specific examples of crosslinkable thermoset monomers suitable for use in exemplary embodiments include, but are not necessarily limited to, the compounds of Formulae 3, 4 and 5:

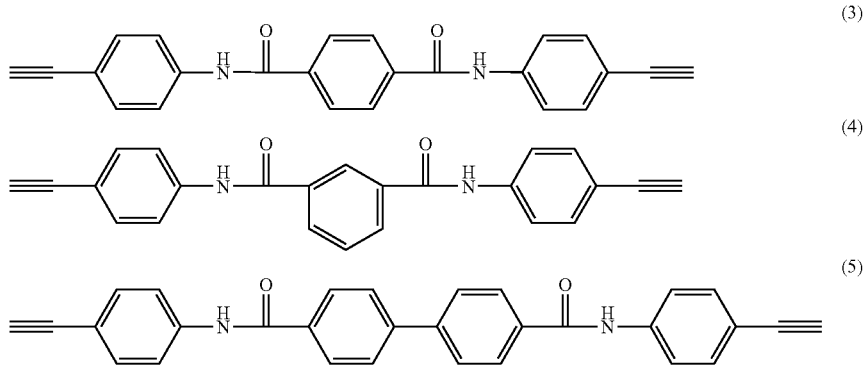

boxylic acid. The liquid crystal polymer may contain two or more of the structural units derived from the aromatic dicarboxylic acids.

Examples of suitable aromatic diamines and hydroxyamines include but are not limited to 3-aminophenol, 4-aminophenol, 1,4-phenylenediamine and 1,3-phenylenediamine. The liquid crystal polymer may contain two or more of the structural units derived from the aromatic diamines and hydroxyamines.

Examples of suitable aromatic aminocarboxylic acids include but are not limited to 3-aminobenzoic acid, 4-aminobenzoic acid and 6-amino-2-naphthoic acid. The liquid crystal polymer may contain two or more of the structural units derived from the aromatic aminocarboxylic acids.

The soluble liquid crystal polymer of the composition contains at least one structural unit selected from the following units 1, 2, 3 and 4:

—O—$Ar_1$—CO—  (1)

wherein $Ar_1$ is 1,4-phenylene, 2,6-naphthylene or 4,4-biphenylene;

—CO—$Ar_2$—CO—  (2)

wherein $Ar_2$ is 1,4-phenylene, 1,3-phenylene or 2,6-naphthylene;

—X—$Ar_3$—Y—  (3)

wherein X is NH, $Ar_3$ is 1,4-phenylene, 2,6-naphthylene 4,4-biphenylene or 1,3-phenylene, and Y is O or NH; and —NH—$Ar_4$—CO—  (4)

wherein $Ar_4$ is 1,4-phenylene, 2,6-naphthylene 4,4-biphenylene or 1,3-phenylene.

It is to be understood that the liquid crystal polymer can contain structural units other than the units 1, 2, 3 and 4.

The structural units 1, 2, 3 and 4 are constituents for the synthesis of the liquid crystal polymer. The structural unit 1 is one derived from an aromatic hydroxycarboxylic acid, the structural unit 2 is one derived from an aromatic dicarboxylic acid, the structural unit 3 is one derived from an aromatic diamine or hydroxyamine, and the structural unit 4 is one derived from an aromatic aminocarboxylic acid.

Examples of suitable aromatic hydroxycarboxylic acids include but are not limited to p-hydroxybenzoic acid, 2-hydroxy-6-naphthoic acid and 4-hydroxy-4'-biphenylcarboxylic acid. The liquid crystal polymer may contain two or more of the structural units derived from the aromatic hydroxycarboxylic acids.

Examples of suitable aromatic dicarboxylic acids include but are not limited to terephthalic acid, isophthalic acid, 2,6-naphthalenedicarboxylic acid and diphenyl ether-4,4'-dicar- There is no particular restriction on the method of preparing the liquid crystal polymer. For example, the liquid crystal polymer can be prepared by acylating a phenolic hydroxyl group of an aromatic hydroxycarboxylic acid, from which the structural unit 1 is derived, with an amino group of an aromatic hydroxylamine or diamine, from which the structural unit 3 is derived, in an excess of a fatty acid anhydride to obtain a corresponding acyl compound, and melt-polycondensing (i.e. transesterifying) the acyl compound with an aromatic dicarboxylic acid, from which the structural unit 2 is derived.

The molecular weight of the liquid crystal polymer is preferably in the range of 5,000 to 500,000, but is not particularly limited to this range.

The soluble liquid crystal thermoset oligomer is composed of a liquid crystal oligomer as a backbone and terminal crosslinking groups. The liquid crystal oligomer backbone may contain at least one of the following structural units 6:

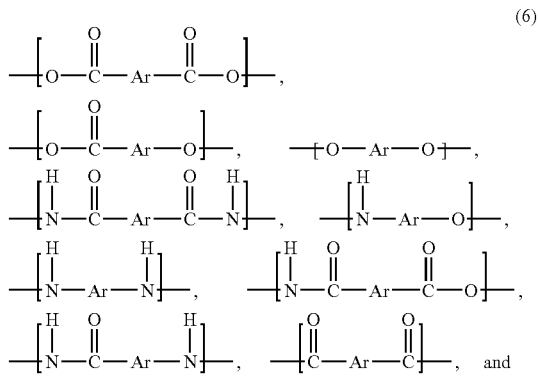

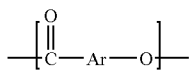

wherein each Ar is selected from the group consisting of the following units 7:

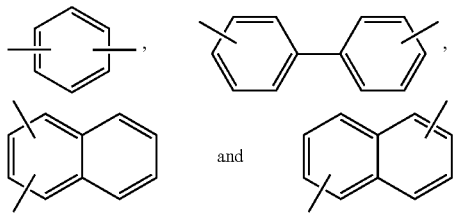

(7)

The same or different crosslinking groups may be introduced at both ends of the backbone. Such crosslinking groups include substituted and unsubstituted acetylene groups, substituted and unsubstituted maleimide groups, substituted and unsubstituted nadimide groups, substituted and unsubstituted phthalimide groups, substituted and unsubstituted propagyl ether groups, substituted and unsubstituted benzocyclobutene groups and substituted and unsubstituted cyanate groups.

The composition may further comprise an aprotic solvent suitable for solvent casting to prevent a deterioration in mechanical properties due to the anisotropicity of the liquid crystal.

No particular limitation is imposed on the kind of the aprotic solvent. The aprotic solvent can be selected from N,N-dimethylacetamide, N-methylpyrrolidone, N-methylcaprolactam, N,N-dimethylformamide, N,N-diethylformamide, N,N-diethylacetamide, N-methylpropionamide, dimethylsulfoxide, γ-butyrolactone, dimethylimidazolidinone, tetramethylphosphoramide, and ethyl cellosolve acetate. These solvents may be used alone or as a mixture of two or more thereof.

In one exemplary embodiment, the composition may comprise the crosslinkable thermoset monomer, the soluble liquid crystal polymer and the aprotic solvent.

In another exemplary embodiment, the composition may comprise the crosslinkable thermoset monomer, the soluble liquid crystal thermoset oligomer and the aprotic solvent.

Optionally, the composition may comprise one or more additives selected from fillers, softeners, plasticizers, lubricants, antistatic agents, colorants, antioxidants, heat stabilizers, light stabilizers and UV absorbers so long as the objects of the invention can be accomplished. Examples of suitable fillers include organic fillers, such as epoxy, melamine, urea, benzoguanamine and styrene resin powders, and inorganic fillers, such as silica, alumina, titanium oxide, zirconia, kaolin, calcium carbonate and calcium phosphate.

The composition can be used as a next-generation packaging material due to its high heat resistance and low thermal expansion properties. The composition can be molded into a board or prepared into a varnish for impregnation or coating applications. Other applications of the composition include laminates, printed boards, layers of multilayer boards, resin-coated copper foils, copper clad laminates, polyimide films, TAB films and prepregs, but are not limited thereto.

For example, a board can be produced by casting the composition, which comprises the crosslinkable thermoset monomer, the soluble liquid crystal polymer, the soluble liquid crystal thermoset oligomer and the aprotic solvent, on a substrate to form a thin film and curing the thin film at high temperature. The solids content of the composition can be increased due to high solubility of the crosslinkable thermoset monomer.

The production of a board with markedly improved mechanical and thermal properties can be achieved by the use of the composition comprising the crosslinkable thermoset monomer, the soluble liquid crystal polymer and the solvent because the crosslinkable thermoset monomer has the ability to form a high-density crosslinked structure after curing. FIG. 1 schematically illustrates a structure after the composition comprising the crosslinkable thermoset monomer, the soluble liquid crystal polymer and the solvent is applied to a substrate, followed by curing. Referring to FIG. 1, after curing, the crosslinkable thermoset monomer is formed into a three-dimensional network structure and the liquid crystal polymer chains are distributed in the network structure to form an interpenetrating-network structure as a whole.

Figure 2:
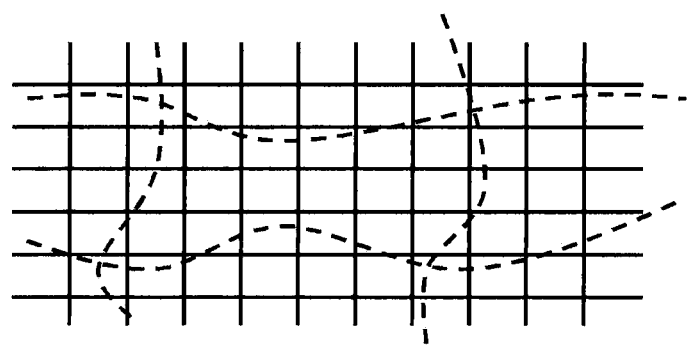
FIG. 2 is an exemplary schematic diagram illustrating a structure after a composition comprising a crosslinkable thermoset monomer, a soluble liquid crystal thermoset oligomer and a solvent is applied to a substrate and cured.

On the other hand, the terminal reactive groups of the liquid crystal thermoset oligomer react with the crosslinkable thermoset monomer. The composition using the liquid crystal thermoset oligomer instead of the liquid crystal polymer is applied and cured to form a structure different from the interpenetrating-network structure. FIG. 2 schematically illustrates a structure after the composition comprising the crosslinkable thermoset monomer, the soluble liquid crystal thermoset oligomer and the solvent is applied to a substrate, followed by curing. Referring to FIG. 2, after curing, the crosslinkable thermoset monomer is formed into a three-dimensional network structure and the liquid crystal thermoset oligomer chains intersect in the network structure to form a crosslinked structure as a whole.

A printed circuit board is generally produced by impregnating a glass fiber with a thermosetting resin, e.g., an epoxy resin, to produce a prepreg and laminating a copper foil on the prepreg. In the case where a typical soluble liquid crystal polymer resin is used to produce a prepreg, the liquid crystal polymer must be dissolved in a suitable solvent to prepare a high-concentration varnish, which is then impregnated into a glass fiber. However, the high molecular weight of the liquid crystal polymer makes it difficult to increase the solids content of the varnish at an optimum viscosity. As a result, there is a limitation in increasing the amount of the resin impregnated into a glass fiber.

A prepreg produced using the composition, which comprises the crosslinkable thermoset monomer having acetylene groups as crosslinking groups introduced at both ends of the backbone, has several advantages over a prepreg produced using a conventional liquid crystal polymer. Specifically, a varnish having a high solids content can be prepared using the composition to facilitate impregnation of the composition into a glass fiber. In addition, the prepreg produced using the composition is thermally stable and has a low coefficient of thermal expansion after curing.

A prepreg can be produced by impregnating a glass fiber with the composition and removing the aprotic solvent. The impregnation can be carried out by any technique known in the art, such as dip coating or roll coating.

The solids content of the composition may be between 10 and 70 parts by weight, based on 100 parts by weight of the composition. When the solids content is less than 10 parts by weight, it is difficult to impregnate an appropriate amount of the resin into a glass fiber. Meanwhile, when the solids content is more than 70 parts by weight, the composition is not readily impregnated into a glass fiber due to its high viscosity.

A copper clad laminate can be produced by applying the composition to a copper foil or casting the composition on a copper foil, removing the solvent, followed by annealing. The solvent is preferably removed by evaporation. The evaporation is carried out under reduced pressure or by ventilation.

Examples of suitable techniques for applying the composition include, but are not necessarily limited to, roll coating, dip coating, spray coating, spin coating, curtain coating, slot coating and screen printing. It is preferred to remove fine impurities contained in the composition by filtration before application to or casting on a copper foil.

A better understanding of exemplary embodiments will be described in more detail with reference to the following examples. However, these examples are given merely for the purpose of illustration and are not to be construed as limiting the scope of the embodiments.

EXAMPLES

Synthesis Example 1

Synthesis of Crosslinkable Thermoset Monomer (LCT-1)

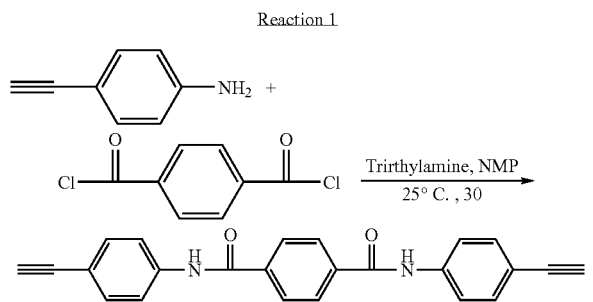

As depicted in Reaction 1, N,N'-bis(4-ethynylphenyl) terephthalamide ($M_W$=364 g/mol) was synthesized from 4-ethynylaniline and terephthaloyl dichloride.

First, a three-neck round-bottom flask equipped with a dropping funnel was flame-dried to remove moisture contained therein. 8.66 g of 4-ethynylaniline was dissolved in 8.66 ml of N-methyl-2-pyrrolidinone in the flask, and then 5.06 ml of triethylamine was added thereto. The mixture was dissolved with stirring at room temperature for 10 minutes. To the solution was added dropwise a solution of 5 g of terephthaloyl dichloride in 5 ml of N-methyl-2-pyrrolidinone through the dropping funnel over a period of 10 minutes. The resulting mixture was allowed to react with stirring for 30 minutes. After completion of the reaction, an aqueous HCl solution was added to the reaction solution to remove unreacted 4-ethynylaniline and salts, and the resulting mixture was passed through filter paper. The filtered crude product was washed with an aqueous $NaHCO_3$ solution to remove unreacted terephthaloyl dichloride, washed with deionized water, and dried to afford the desired product (yield>90%) as a pale yellow powder, represented by Formula 3:

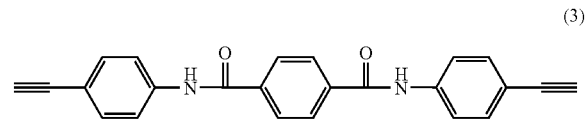

Figure 3:
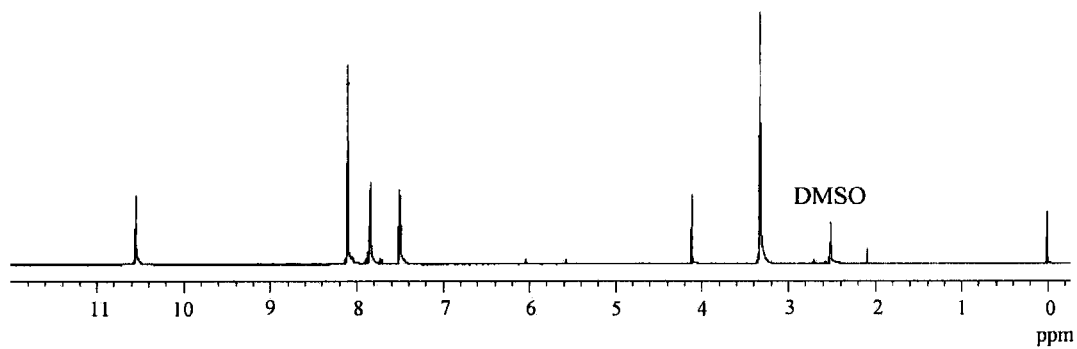
FIG. 3 is a $^1$H-NMR spectrum of a crosslinkable thermoset monomer prepared in Synthesis Example 1.

The progress of the reaction and the purity of the product were confirmed by TLC on a 0.25 mm thick silica gel plate (Merck) with a 254 nm indicator. The structure of the product was identified using a Varian Unity Inova Spectrometer (500-MHz, $d_6$-DMSO). The obtained $^1$H-NMR spectrum is shown in FIG. 3. Referring to FIG. 3, a peak corresponding to the hydrogen atoms of the amide groups was observed at δ 10.54. The NMR analysis indicates that the product was synthesized from 4-ethynylaniline and terephthaloyl dichloride.

Synthesis Example 2

Synthesis of Crosslinkable Thermoset Monomer (LCT-2)

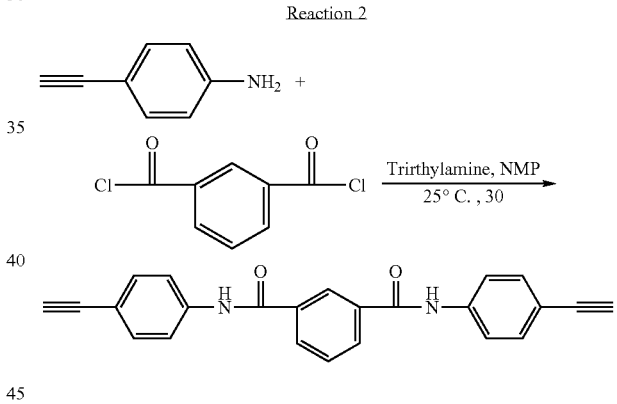

As depicted in Reaction 2, N,N'-bis(4-ethynylphenyl) isophthalamide of Formula 4 ($M_W$=363 g/mol) was synthesized (yield>90%).

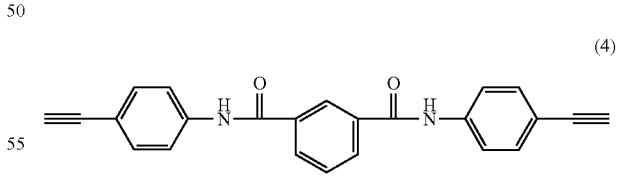

Figure 4:
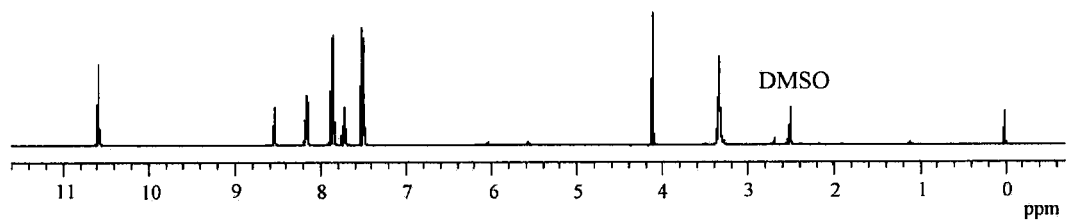
FIG. 4 is a $^1$H-NMR spectrum of a crosslinkable thermoset monomer prepared in Synthesis Example 2.

Specifically, the product was prepared in the same manner as in Synthesis Example 1 except that 5 g of isophthaloyl dichloride was used instead of terephthaloyl dichloride. The structure of the product was identified by $^1$H-NMR. The obtained $^1$H-NMR spectrum is shown in FIG. 4. Referring to FIG. 4, a peak corresponding to the hydrogen atoms of the amide groups was observed at δ 10.56. The NMR analysis indicates that the product was synthesized from 4-ethynylaniline and isophthaloyl dichloride.

Synthesis Example 3

Synthesis of Crosslinkable Thermoset Monomer (LCT-3)

Reaction 3

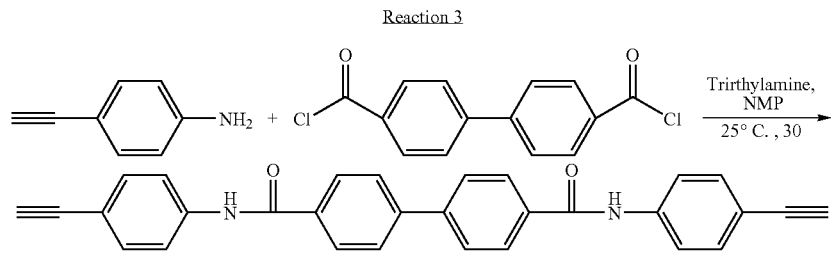

As depicted in Reaction 3, N,N'-bis(4-ethynylphenyl)biphenyl-4,4'-dicarboxyamide) of Formula 5 ($M_W$=440 g/mol) was synthesized (yield>90%).

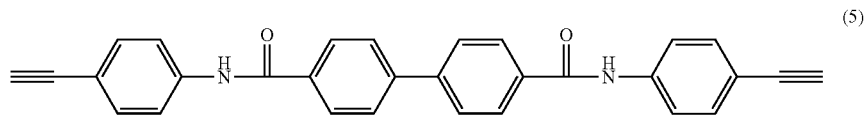 [SMILES: C#Cc1ccc(NC(=O)c2ccc(-c3ccc(C(=O)Nc4ccc(C#C)cc4)cc3)cc2)cc1]

(5)

Figure 5:
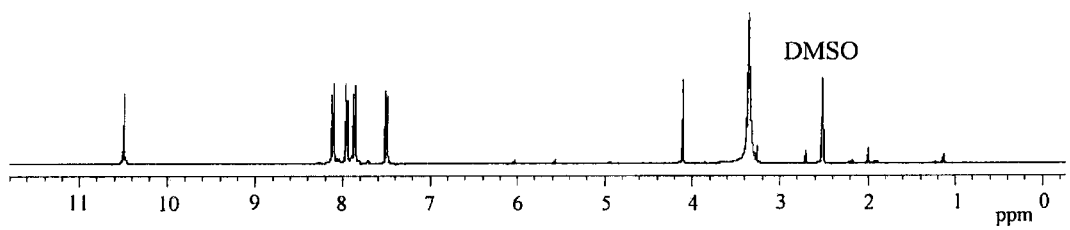
FIG. 5 is a $^1$H-NMR spectrum of a crosslinkable thermoset monomer prepared in Synthesis Example 3.

Specifically, the product was synthesized in the same manner as in Synthesis Example 1 except that 6.3 g of 4-ethynylaniline was used and 5 g of biphenyl-4,4'-dicarbonyl dichloride was used instead of terephthaloyl dichloride. The structure of the product was identified by $^1$H-NMR. The obtained $^1$H-NMR spectrum is shown in FIG. 5. Referring to FIG. 5, a peak corresponding to the hydrogen atoms of the amide groups was observed at δ 10.43. The NMR analysis indicates that the product was synthesized from 4-ethynylaniline and biphenyl-4,4'-dicarbonyl dichloride.

Figure 6:
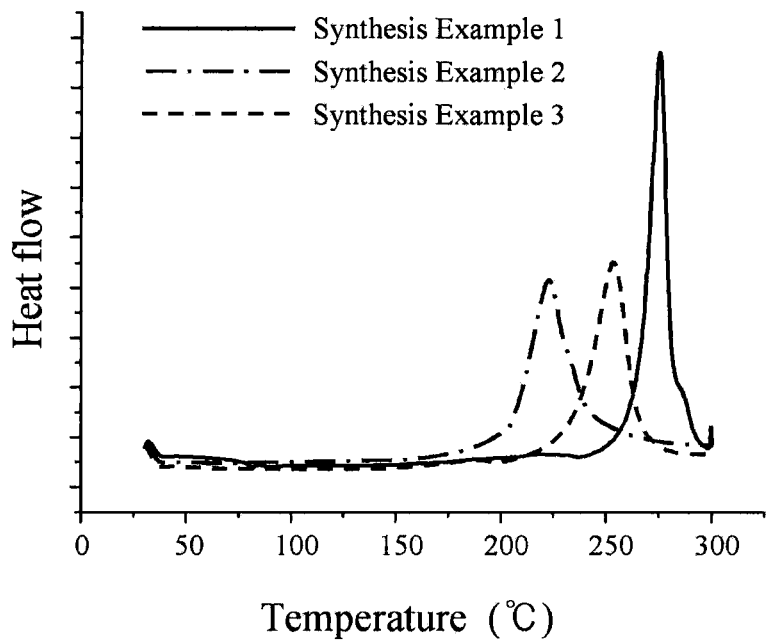
FIG. 6 is a graph showing the results of differential scanning calorimetry (DSC) for crosslinkable thermoset monomers prepared in Synthesis Examples 1, 2 and 3.

The thermal properties of LCT-1, LCT-2 and LCT-3 were analyzed under a nitrogen atmosphere by differential scanning calorimetry (DSC, TA Instruments DSC 2010). The obtained DSC curves are shown in FIG. 6. The graph of FIG. 6 shows that exothermic peaks corresponding to thermal curing of LCT-1, LCT-2 and LCT-3 were observed at 275° C., 223° C. and 253° C., respectively, demonstrating that LCT-1, LCT-2 and LCT-3 can be used under thermal treatment temperature conditions of compositions for the production of printed circuit boards.

Synthesis Example 4

Synthesis of Liquid Crystal Polymer 8.3 g (0.05 mol) of isophthalic acid, 18.8 g (0.1 mol) of 6-hydroxy-2-naphthoic acid, 5.5 g (0.05 mol) of 4-aminophenol and 32.7 g (0.32 mol) of acetic anhydride were put into a 500 ml flask equipped with a condenser and a mechanical stirrer. The mixture was slowly heated to 150° C. under a nitrogen atmosphere. The reaction proceeded for 4 hours while maintaining the reaction temperature at 150° C. to complete the acetylation of the reactants by the acetic anhydride. Subsequently, the reaction mixture was heated to 300° C. while removing acetic acid and unreacted acetic anhydride. The reaction was continued for one hour to prepare polyamide-ester as a soluble liquid crystal polymer.

Example 1

The liquid crystal polymer (polyamide-ester) prepared in Synthesis Example 4 and LCT-1 prepared in Synthesis Example 1 were mixed together in weight ratios of 90:10, 80:20 and 70:30. The thermal properties of the mixtures were analyzed under a nitrogen atmosphere by differential scanning calorimetry (DSC, TA Instruments DSC 2010). The obtained DSC curves are shown in FIG. 7.

Comparative Example 1

The thermal properties of the liquid crystal polymer (polyamide-ester) prepared in Synthesis Example 4 were analyzed under a nitrogen atmosphere by differential scanning calorimetry (DSC, TA Instruments DSC 2010). The obtained DSC curve is shown in FIG. 7.

Figure 7:
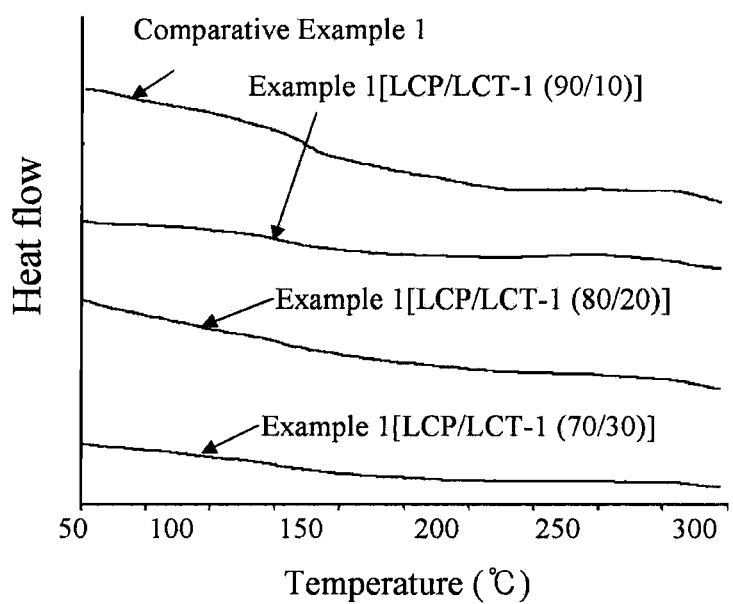
FIG. 7 is a graph showing the results of differential scanning calorimetry (DSC) for compositions prepared in Example 1 and Comparative Example 1.

It was confirmed from graph of FIG. 7 that the glass transition temperature ($T_g$) of the soluble liquid crystal polymer prepared in Comparative Example 1 was observed at 142° C. whereas no glass transition temperatures were observed in the mixtures of the soluble liquid crystal polymer and LCT-1. This is thought to be because LCT-1 was thermally cured and incorporated between the soluble liquid crystal polymer chains so that the mixtures had a glass transition temperature higher than 300° C. or no glass transition temperature.

Example 2

Figure 8:
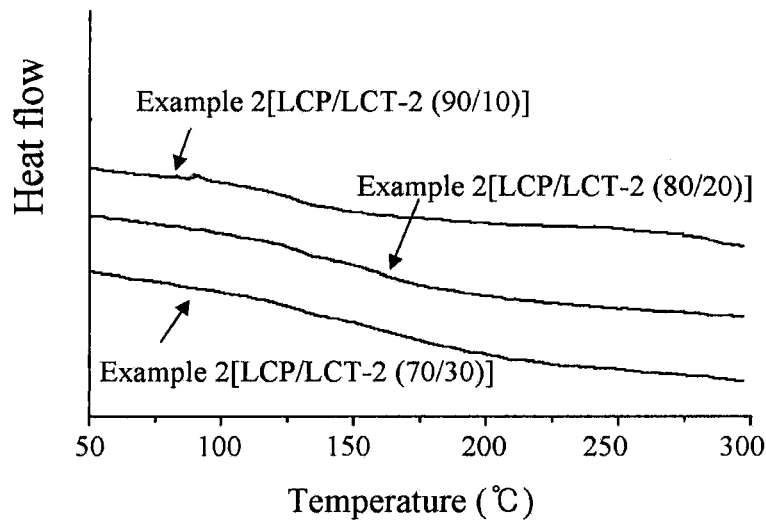
FIG. 8 is a graph showing the results of differential scanning calorimetry (DSC) for compositions prepared in Example 2.

The liquid crystal polymer (polyamide-ester) prepared in Synthesis Example 4 and LCT-2 prepared in Synthesis Example 2 were mixed together in weight ratios of 90:10, 80:20 and 70:30. The thermal properties of the mixtures were analyzed under a nitrogen atmosphere by differential scanning calorimetry (DSC, TA Instruments DSC 2010). The obtained DSC curves are shown in FIG. 8.

Example 3

Figure 9:
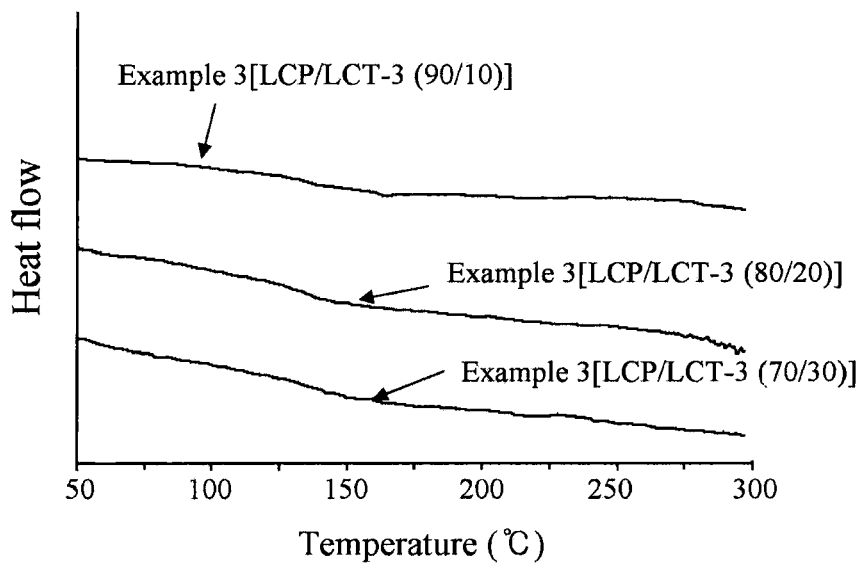
FIG. 9 is a graph showing the results of differential scanning calorimetry (DSC) for compositions prepared in Example 3.

The liquid crystal polymer (polyamide-ester) prepared in Synthesis Example 4 and LCT-1 prepared in Synthesis Example 3 were mixed together in weight ratios of 90:10, 80:20 and 70:30. The thermal properties of the mixtures were analyzed under a nitrogen atmosphere by differential scanning calorimetry (DSC, TA Instruments DSC 2010). The obtained DSC curves are shown in FIG. 9.

As in Example 1, no distinct glass transition temperatures ($T_g$) were observed below 300° C. in the mixtures of Example 2 and Example 3. This is thought to be because LCT-1 or LCT-2 was thermally cured and incorporated between the soluble liquid crystal polymer chains so that the mixtures had a glass transition temperature higher than 300° C. or no glass transition temperature.

Example 4

Figure 10:
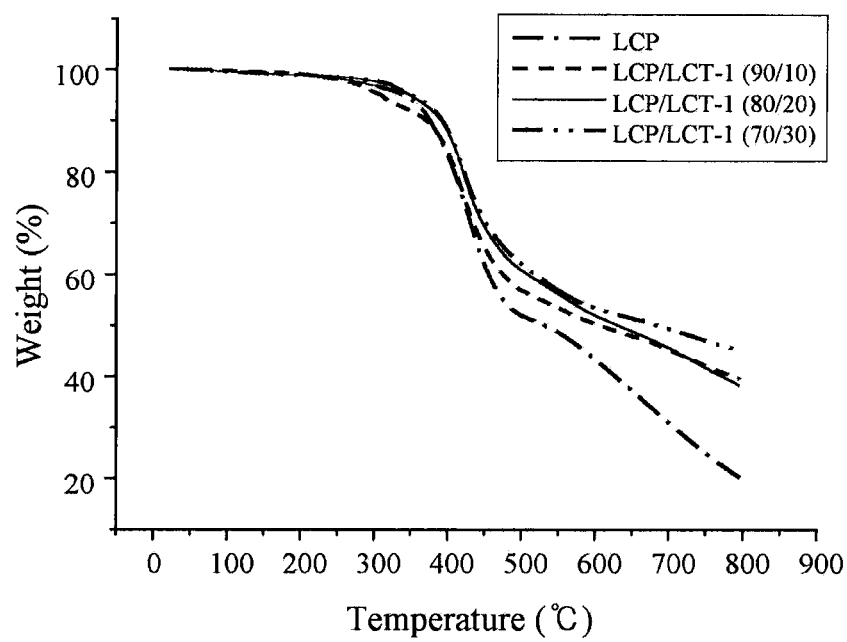
FIG. 10 is a graph showing the results of thermogravimetric analysis (TGA) for compositions prepared in Example 4.

The liquid crystal polymer (polyamide-ester) prepared in Synthesis Example 4 and LCT-1 prepared in Synthesis Example 1 were mixed together in weight ratios of 90:10, 80:20 and 70:30. The weight loss (%) of each mixture was measured using a thermogravimetric analyzer (TGA 2050, TA Instruments). The obtained TGA curves are shown in FIG. 10. For comparison, the weight loss of the liquid crystal polymer prepared in Synthesis Example 4 was measured (FIG. 10).

As is evident from the graph of FIG. 10, the initial thermal decomposition temperature of the soluble liquid crystal polymer was 352° C., there was no change in the thermal decomposition temperature of the mixture (90:10 (w/w)) of the soluble liquid crystal polymer and LCT-1, and the mixtures of the soluble liquid crystal polymer and LCT-1 in the weight ratios of 80:20 and 70:30 were thermally decomposed at 373° C., which is higher by about 21° C. than the thermal decomposition temperature of the mixture (90:10 (w/w)). These results are believed to be because the thermoset monomer was thermally cured to improve the thermal properties of the soluble liquid crystal polymer. It was also confirmed that decrements in the thermal decomposition weight of the mixtures were reduced and the thermal stability of the mixtures was improved with increasing weight ratio of the thermoset monomer.

Example 5

Figure 11:
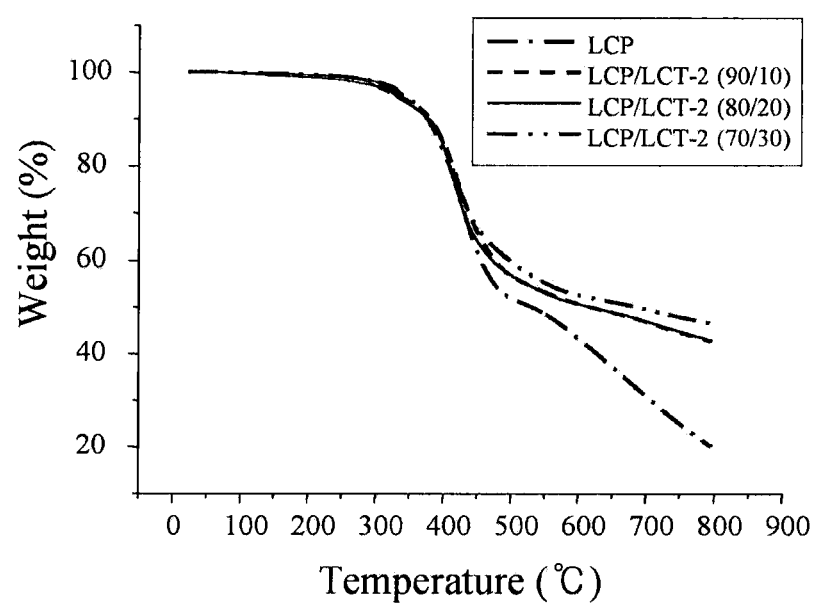
FIG. 11 is a graph showing the results of thermogravimetric analysis (TGA) for compositions prepared in Example 5.

The liquid crystal polymer (polyamide-ester) prepared in Synthesis Example 4 and LCT-2 prepared in Synthesis Example 2 were mixed together in weight ratios of 90:10, 80:20 and 70:30. The weight loss (%) of each mixture was measured using a thermogravimetric analyzer (TGA 2050, TA Instruments). The obtained TGA curves are shown in FIG. 11. For comparison, the weight loss of the liquid crystal polymer prepared in Synthesis Example 4 was measured (FIG. 11).

Example 6

Figure 12:
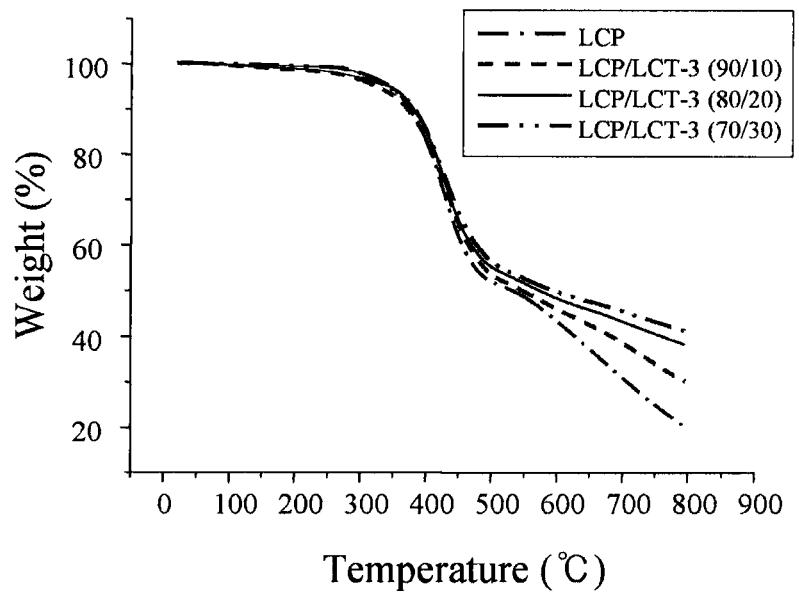
FIG. 12 is a graph showing the results of thermogravimetric analysis (TGA) for compositions prepared in Example 6.
Figure 13:
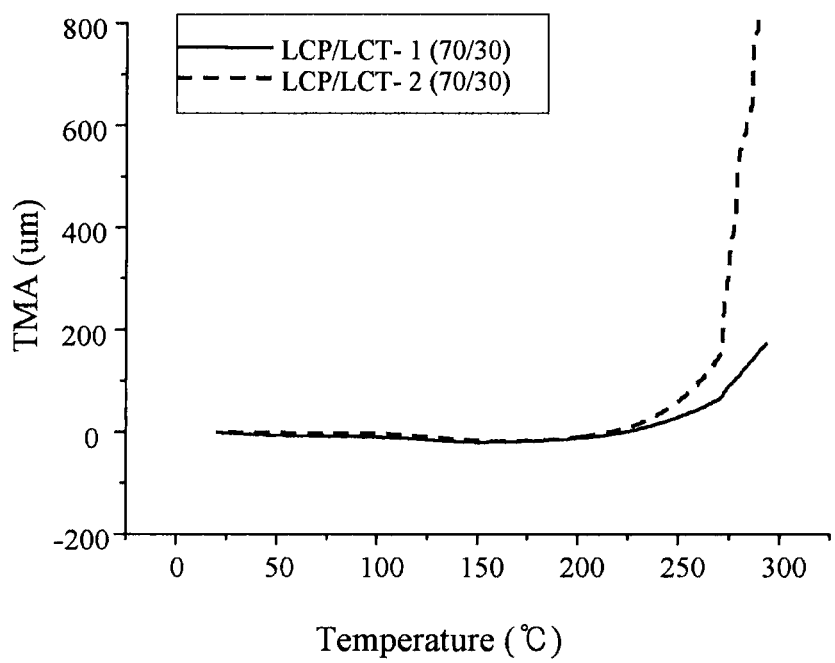
FIG. 13 is a graph showing the results of thermomechanical analysis for free-standing films produced in Examples 8 and 9.

The liquid crystal polymer (polyamide-ester) prepared in Synthesis Example 4 and LCT-3 prepared in Synthesis Example 3 were mixed together in weight ratios of 90:10, 80:20 and 70:30. The weight loss (%) of each mixture was measured using a thermogravimetric analyzer (TGA 2050, TA Instruments). The obtained TGA curves are shown in FIG. 12. For comparison, the weight loss of the liquid crystal polymer prepared in Synthesis Example 4 was measured (FIG. 12).

Referring to the graphs of FIGS. 11 and 12, there were no significant changes in the thermal decomposition initiation temperature of the mixtures, but decrements in the thermal decomposition weight of the mixtures were lowered. These results lead to the conclusion that thermal curing of the thermoset monomers enhanced the physical properties and improved the thermal stability of the mixtures.

Example 7

The amounts of carbon residue in the soluble liquid crystal polymer and the mixtures (70/30 (w/w)) of the soluble liquid crystal polymer with LCT-1, LCT-2 and LCT-3 were measured at 800° C. The results are shown in Table 1. The results show that the amount of carbon residue was 20% in the soluble liquid crystal polymer whereas the amounts of carbon residue were relatively large in the mixtures of the soluble liquid crystal polymer with LCT-1 (46%), LCT-2 (46%) and LCT-3 (41%). That is, the blending of the soluble liquid crystal polymer and the crosslinkable thermoset monomers increased the thermal decomposition temperature of the mixtures and the amounts of carbon left at high temperature, indicating that the crosslinkable thermoset monomers contributed to improvements in the mechanical strength and thermal stability of the mixtures.

TABLE 1

| Sample | Decomposition temp. (° C.) | Amount of carbon residue (%) |
| --- | --- | --- |
| LCP | 352 | 20 |
| LCP/LCT-1 (70/30) | 373 | 46 |
| LCP/LCT-2 (70/30) | 352 | 46 |
| LCP/LCT-3 (70/30) | 352 | 41 |

Example 8

Production of Free-Standing Film

An electrodeposited copper foil was cut to a size of 1 cm (w)×3 cm (1) and five polyimide tapes were sequentially attached to the four sides of the copper foil. A hole (4 mm (w)×20 mm (1)) was formed at the center of the copper foil to construct a mold.

A mixture of the soluble liquid crystal polymer and LCT-1 (70:30 (w/w)) was dissolved in 6.5 ml of NMP. The solution was heated to 110° C., printed on the mold, dried in an oven at 80° C. at reduced pressure to completely remove the NMP, and thermally treated at 280° C. for 2 hours. Subsequently, the polyimide tapes were removed from the copper foil, followed by etching in a 30% aqueous nitric acid solution to produce a free-standing film (4 mm (w)×20 mm (1)).

Example 9

Production of Free-Standing Film

A free-standing film was produced in the same manner as in Example 8 except that 3.5 g of a mixture of the soluble liquid crystal polymer and LCT-2 (70:30 (w/w)) was used instead of the mixture of the soluble liquid crystal polymer and LCT-1 (70:30 (w/w)).

Comparative Example 2

Production of Free-Standing Film

The procedure of Example 8 was repeated except that 3.5 g of the soluble liquid crystal polymer was used instead of the mixture of the soluble liquid crystal polymer and LCT-1 (70:30 (w/w)).

Comparative Example 3

Production of Free-Standing Film

The procedure of Example 8 was repeated except that 3.5 g of a mixture of the soluble liquid crystal polymer and LCT-1 (90:10 (w/w)) was used instead of the mixture of the soluble liquid crystal polymer and LCT-1 (70:30 (w/w)).

A thermomechanical analyzer (TMA 2940, TA Instruments) was used to confirm as to whether or not free-standing films were formed in Examples 8 and 9 and Comparative Examples 2 and 3 and to calculate the coefficients of thermal expansion of the free-standing films formed in Examples 8 and 9. The results are shown in Table 2. Unlike in Examples 8 and 9, no films were formed in Comparative Examples 2 and 3. The results reveal that the film formation was determined depending on the kind and structure of the thermoset monomers used, and that the weight ratio of the thermoset monomers affected the mechanical strength and physical properties of the films. In addition, it can be concluded that the crosslinkable thermoset monomer was blended between the soluble liquid crystal polymer chains and thermally cured to improve the rigidity of the liquid crystal polymer.

TABLE 2

| Sample | Formation of free-standing film | Coefficient of thermal expansion (ppm/° C.) |
| --- | --- | --- |
| Example 8 | ○ | 5.3 |
| Example 9 | ○ | 8.1 |
| Comparative Example 2 | X | — |
| Comparative Example 3 | X | — |

Thermomechanical analysis (TMA) was conducted on the free-standing films of Examples 8 and 9. The obtained TMA curves are shown in Table 13. The graph shows that the film of Example 8 was thermally expanded in the range of 232-300° C., and the film of Example 9 began to be thermally expanded at 228° C. and was finally broken at 250° C.

Although exemplary embodiments have been described in detail with reference to the foregoing preferred embodiments, those skilled in the art will readily appreciate that many modifications and variations can be made without departing from the spirit and scope of the invention. Therefore, such modifications and variations should be construed as falling within the scope of the invention.

What is claimed is:

1. A crosslinkable thermoset monomer having acetylene groups introduced at both ends of the backbone, represented by following formula:

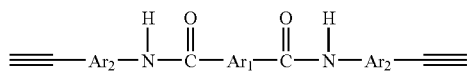

wherein $Ar_1$ and $Ar_2$ are each independently a divalent aromatic organic group including at least one structural unit selected from the group consisting of

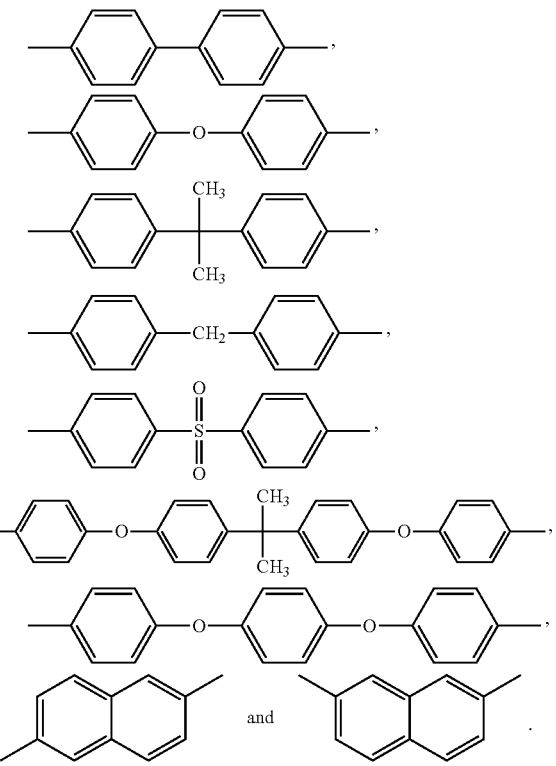

2. A composition for producing a printed circuit board, comprising:

a crosslinkable thermoset monomer having acetylene groups introduced at both ends of the backbone, represented by following formula:

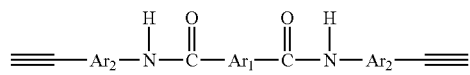

wherein $Ar_1$ and $Ar_2$ are each independently a divalent aromatic organic group including at least one structural unit selected from the group consisting of

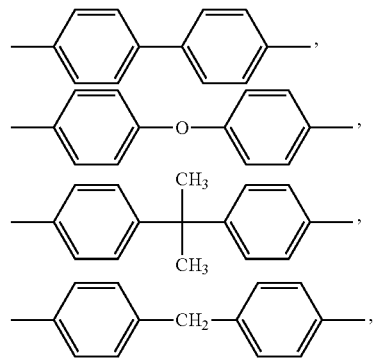

-continued

[structure: bis(phenyl)sulfone]

[structure: -Ph-O-Ph-C(CH3)2-Ph-O-Ph-]

[structure: -Ph-O-Ph-O-Ph-]

[structure: 2,6-naphthylene] and

[structure: 2,7-naphthylene];

and
a soluble liquid crystal polymer or a soluble liquid crystal thermoset oligomer.

3. The composition of claim 2, wherein the crosslinkable thermoset monomer and the soluble liquid crystal polymer or the soluble liquid crystal thermoset oligomer are present in a weight ratio of 5:95 to 70:30.

4. The composition of claim 2, wherein the soluble liquid crystal polymer contains at least one structural unit selected from the group consisting of —O—$Ar_1$—CO— wherein $Ar_1$ is 1,4-phenylene, 2,6-naphthylene or 4,4-biphenylene;

—CO—$Ar_2$—CO— wherein $Ar_2$ is 1,4-phenylene, 1,3-phenylene or 2,6-naphthylene;

—X—$Ar_3$—Y— wherein X is NH, $Ar_3$ is 1,4-phenylene 1,3-phenylene, and Y is O or NH; and

—NH—$Ar_4$—CO— wherein $Ar_1$ is 1,4-phenylene or 1,3-phenylene.

5. The composition of claim 2, wherein the soluble liquid crystal thermoset oligomer contains at least one of the following structural units selected from the group consisting of:

[structures: —(O—CO—Ar—CO—O)—, —(O—CO—Ar—O)—,
—(O—Ar—O)—, —(N(H)—CO—Ar—CO—N(H))—,
—(N(H)—Ar—O)—, —(N(H)—Ar—N(H))—,
—(N(H)—CO—Ar—CO—O)—, —(N(H)—CO—Ar—N(H))—,
—(CO—Ar—CO)—, and —(CO—Ar—O)—]

wherein each Ar is selected from the group consisting of:

[structures: 1,4-phenylene, biphenylene, naphthylene, and naphthylene]

6. The composition of claim 2, wherein the soluble liquid crystal thermoset oligomer has the same or different crosslinking groups introduced at both ends thereof, and each of the crosslinking groups is selected from substituted and unsubstituted acetylene groups, substituted and unsubstituted maleimide groups, substituted and unsubstituted nadimide groups, substituted and unsubstituted phthalimide groups, substituted and unsubstituted propagyl ether groups, substituted and unsubstituted benzocyclobutene groups and substituted and unsubstituted cyanate groups.

7. The composition of claim 2 further comprising an aprotic solvent.

8. The composition of claim 7, wherein the composition has a solids content of 10 to 70 parts by weight, based on 100 parts by weight of the composition.

9. A board comprising the composition of claim 2.

10. The board of claim 9, wherein the board is selected from the group consisting of a printed circuit board, a copper foil, a copper clad laminate, and a prepreg.

11. The composition of claim 2, wherein the soluble liquid crystal polymer contains at least one structural unit of —NH—$Ar_4$—CO—, wherein $Ar_4$ is 1,4-phenylene or 1,3-phenylene.

12. A composition for producing a printed circuit board, comprising:
a crosslinkable thermoset monomer having acetylene groups introduced at both ends of the backbone, represented by following formula:

$$\equiv\!\!-\!Ar_2\!-\!N(H)\!-\!C(=\!O)\!-\!Ar_1\!-\!C(=\!O)\!-\!N(H)\!-\!Ar_2\!-\!\equiv$$

wherein $Ar_1$ and $Ar_2$ are each independently a divalent aromatic organic group including at least one structural unit selected from the group consisting of

[structures: 1,4-phenylene, 1,3-phenylene, biphenylene, diphenyl ether, and bisphenol-A-type]

-continued

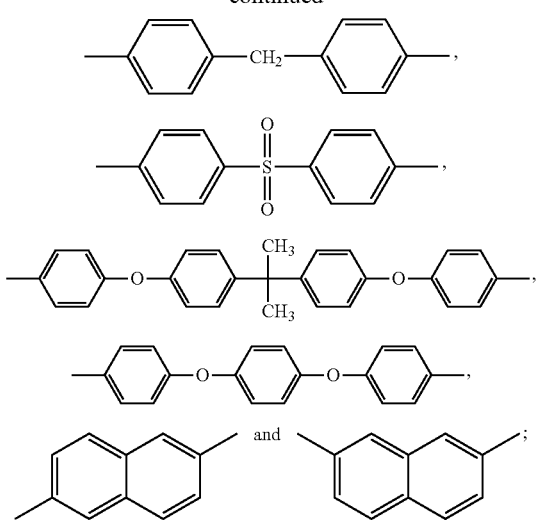

and a soluble liquid crystal thermoset oligomer comprising at least one structural units selected from the group consisting of:

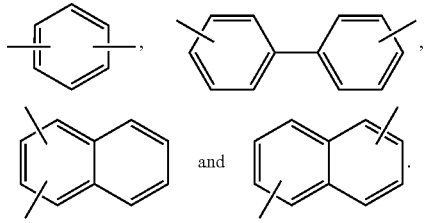

-continued

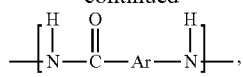

wherein each Ar is selected from the group consisting of:

13. The composition of claim 12, wherein the crosslinkable thermoset monomer and the soluble liquid crystal thermoset oligomer are present in a weight ratio of 5:95 to 70:30.

14. The composition of claim 12, wherein the soluble liquid crystal thermoset oligomer has the same or different crosslinking groups introduced at both ends thereof, and each of the crosslinking groups is selected from the group consisting of substituted and unsubstituted acetylene groups, substituted and unsubstituted maleimide groups, substituted and unsubstituted nadimide groups, substituted and unsubstituted phthalimide groups, substituted and unsubstituted propagyl ether groups, substituted and unsubstituted benzocyclobutene groups and substituted and unsubstituted cyanate groups.

15. The composition of claim 12, further comprising an aprotic solvent.

16. The composition of claim 12, wherein the composition has a solids content of 10 to 70 parts by weight, based on 100 parts by weight of the composition.

17. A board comprising the composition of claim 12.

18. The board of claim 17, wherein the board is selected from the group consisting of a printed circuit board, a copper foil, a copper clad laminate, and a prepreg.

* * * * *